US012573046B2

(12) United States Patent
Okuda

(10) Patent No.: US 12,573,046 B2
(45) Date of Patent: Mar. 10, 2026

(54) METHODS AND SYSTEMS FOR ANALYZING BRAIN LESIONS FOR THE DIAGNOSIS OF MULTIPLE SCLEROSIS

(71) Applicant: The Board of Regents of The University of Texas System, Austin, TX (US)

(72) Inventor: Darin T. Okuda, Coppell, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 361 days.

(21) Appl. No.: 18/549,673

(22) PCT Filed: Mar. 8, 2022

(86) PCT No.: PCT/US2022/071023
§ 371 (c)(1),
(2) Date: Sep. 8, 2023

(87) PCT Pub. No.: WO2022/192867
PCT Pub. Date: Sep. 15, 2022

(65) Prior Publication Data
US 2024/0153091 A1 May 9, 2024

Related U.S. Application Data

(60) Provisional application No. 63/158,142, filed on Mar. 8, 2021.

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/4842* (2013.01); *G06T 7/20* (2013.01);
(Continued)

(58) Field of Classification Search
None
See application file for complete search history.

(56) References Cited

U.S. PATENT DOCUMENTS

2013/0329973 A1 12/2013 Cao et al.
2019/0197347 A1* 6/2019 Okuda ................... G06V 10/75
(Continued)

FOREIGN PATENT DOCUMENTS

WO WO 2019/165464 8/2019

OTHER PUBLICATIONS

Sethi et al., "Slowly Eroding Lesions in Multiple Sclerosis." Mult Scle. 2017, 23, pp. 464-472. (Year: 2017).*
(Continued)

*Primary Examiner* — SJ Park
*Assistant Examiner* — Caroline E. Depalma
(74) *Attorney, Agent, or Firm* — NORTON ROSE FULBRIGHT US LLP

(57) ABSTRACT

Some methods comprise, for each of one or more lesions of a patients brain, from data taken at first and second times, determining two or more lesion characteristics including a lesion's volume change and whether the lesion moved toward a center of the brain. Some methods comprise, for each lesion, determining whether one or more criteria are satisfied, including a volume-and-displacement-based criterion that is satisfied when the change in the volume of the lesion is less than zero and the lesion moved toward the brain's center or the change in the volume of the lesion is greater than zero and the lesion did not move toward the brain's center. Some methods comprise characterizing whether the patient has multiple sclerosis and/or the progression, regression, or stability of multiple sclerosis based at least in part on the assessment of the one or more criteria for each of the lesion(s).

19 Claims, 6 Drawing Sheets

(51) Int. Cl.
  *G06T 7/20* (2017.01)
  *G06T 7/62* (2017.01)
(52) U.S. Cl.
  CPC ...... *G06T 7/62* (2017.01); *G06T 2207/10088* (2013.01); *G06T 2207/30016* (2013.01); *G06T 2207/30096* (2013.01)

(56) References Cited

U.S. PATENT DOCUMENTS

2019/0370970 A1* 12/2019 Kim ...................... G06T 7/0016
2021/0090259 A1    3/2021 Okuda

OTHER PUBLICATIONS

Ono, Daisuke, et al. "Development of demyelinating lesions in progressive multifocal leukoencephalopathy (PML): Comparison of magnetic resonance images and neuropathology of post-mortem brain." Neuropathology 39.4 (2019): 294-306. (Year: 2019).*

Altay et al., "Reliability of classifying multiple sclerosis disease activity using magnetic resonance imaging in a multiple sclerosis clinic." *JAMA Neurol*. 2013, 70, pp. 338-344.

Bagnato et al., "Evolution of T1 black holes in patients with multiple sclerosis imaged monthly for 4 years." *Brain*. 2003, 126, pp. 1782-1789.

Craggs et al., "Microvascular pathology and morphometrics of sporadic and hereditary small vessel diseases of the brain." *Brain Pathol*. 2014, 24, pp. 495-509.

Dal-Bianco et al., "Slow expansion of multiple sclerosis iron rim lesions: pathology and 7 T magnetic resonance imaging." *Acta Neuropathol*. 2017, 133, pp. 25-42.

Elliott et al., "Chronic white matter lesion activity predicts clinical progression in primary progressive multiple sclerosis." *Brain* 2019, 142, pp. 2787-2799.

Elliott et al., "Slowly expanding/evolving lesions as a magnetic resonance imaging marker of chronic active multiple sclerosis lesions." *Mult Scler*. 2019, 25, pp. 1915-1925.

Frischer et al., "Clinical and pathological insights into the dynamic nature of the white matter multiple sclerosis plaque." *Ann Neurol*. 2015, 78, pp. 710-721.

Hammond et al., "Quantitative in vivo magnetic resonance imaging of multiple sclerosis at 7 Tesla with sensitivity to iron." *Ann Neurol*. 2008, 64, pp. 707-713.

Hansen et al., "Post-gadolinium 3-dimensional spatial, surface, and structural characteristics of glioblastomas differentiate pseudoprogression from true tumor progression." *J Neurooncol*. 2018; 139, pp. 731-738.

Iliff et al., "A paravascular pathway facilitates CSF flow through the brain parenchyma and the clearance of interstitial solutes, including amyloid β." *Sci Transl Med*. 2012, 4: 147ra11, 22 pages.

International Search Report and Written Opinion issued in Corresponding PCT Application No. PCT/US2022/071023, dated Jun. 3, 2022.

Kaunzner et al. "Quantitative susceptibility mapping identifies inflammation in a subset of chronic multiple sclerosis lesions." *Brain*. 2019, 142, pp. 133-145.

Li et al., "Cerebral Small Vessel Disease." *Cell Transplant*. 2018; 27, pp. 1711-1722.

Luchetti et al., "Progressive multiple sclerosis patients show substantial lesion activity that correlates with clinical disease severity and sex: a retrospective autopsy cohort analysis." *Acta Neuropathol*. 2018, 135, pp. 511-528.

Maggi et al., "Paramagnetic Rim Lesions are Specific to Multiple Sclerosis: An International Multicenter 3T MRI Study." *Ann Neurol*. 2020, 88(5), pp. 1034-1042.

Moog et al., "African Americans experience disproportionate neurodegenerative changes in the medulla and upper cervical spinal cord in early multiple sclerosis." *Mult Scler Relat Disord*. 2020, 45, 102429.

Ono et al., "Development of demyelinating lesions in progressive multifocal leukoencephalopathy (PML): Comparison of magnetic resonance images and neuropathology of post-mortem brain" *Neuropathology* 2019, 39, 294-306.

Pantoni L., "Cerebral small vessel disease: from pathogenesis and clinical characteristics to therapeutic challenges." *Lancet Neurol*. 2010, 9, pp. 689-701.

Popescu et al., "Pathogenic implications of distinct patterns of iron and zinc in chronic MS lesions." *Acta Neuropathol*. 2017, 134, pp. 45-64.

Prineas et al., "Immunopathology of secondary-progressive multiple sclerosis." *Ann Neurol*. 2001, 50, pp. 646-657.

Sati et al., "The central vein sign and its clinical evaluation for the diagnosis of multiple sclerosis: a consensus statement from the North American Imaging in Multiple Sclerosis Cooperative." *Nat Rev Neurol*. 2016, 12, pp. 714-722.

Sethi et al., "Slowly eroding lesions in multiple sclerosis." *Mult Scler*. 2017, 23, pp. 464-472.

Sivakolundu et al., "BOLD signal within and around white matter lesions distinguishes multiple sclerosis and non-specific white matter disease: a three-dimensional approach." *J Neurol*. 2020, 267, pp. 2888-2896.

Sivakolundu et al., "Three-Dimensional Lesion Phenotyping and Physiologic Characterization Inform Remyelination Ability in Multiple Sclerosis." *J Neuroimaging*. 2019; 29, 10 pages.

Solomon et al., "Central vessel sign on 3T FLAIR* MRI for the differentiation of multiple sclerosis from migraine." Ann Clin Transl Neurol. 2016, 3, pp. 82-87.

Solomon et al., "The contemporary spectrum of multiple sclerosis misdiagnosis: A multicenter study." *Neurology*. 2016; 87, pp. 1393-1399.

Suthiphosuwan et al., "Paramagnetic Rim Sign in Radiologically Isolated Syndrome." *JAMA Neurol*. 2020, 77, pp. 653-655.

Thompson et al., "Diagnosis of multiple sclerosis: 2017 revisions of the McDonald criteria." *Lancet Neurol*. 2018; 17: 50 pages.

Trapp et al., "Axonal transection in the lesions of multiple sclerosis." *N Engl J Med*. 1998, 338, pp. 278-285.

Wardlaw et al., "Mechanisms of sporadic cerebral small vessel disease: insights from neuroimaging." *Lancet Neurol*. 2013, 12, pp. 483-497.

Zeydan et al., "MS progression is predominantly driven by age-related mechanisms—Commentary." *Mult Scler*. 2019; 25, pp. 906-908.

Zrzavy et al., "Loss of 'homeostatic' microglia and patterns of their activation in active multiple sclerosis." *Brain*. 2017, 140, pp. 1900-1913.

Extended European Search Report issued in corresponding European Application No. 22768209.3, dated Jan. 23, 2025.

Okuda et al., "Utility of shape evolution and displacement in the classification of chronic multiple sclerosis lesions" *Scientific Reports* 2020, 10(1), 8 pages.

* cited by examiner

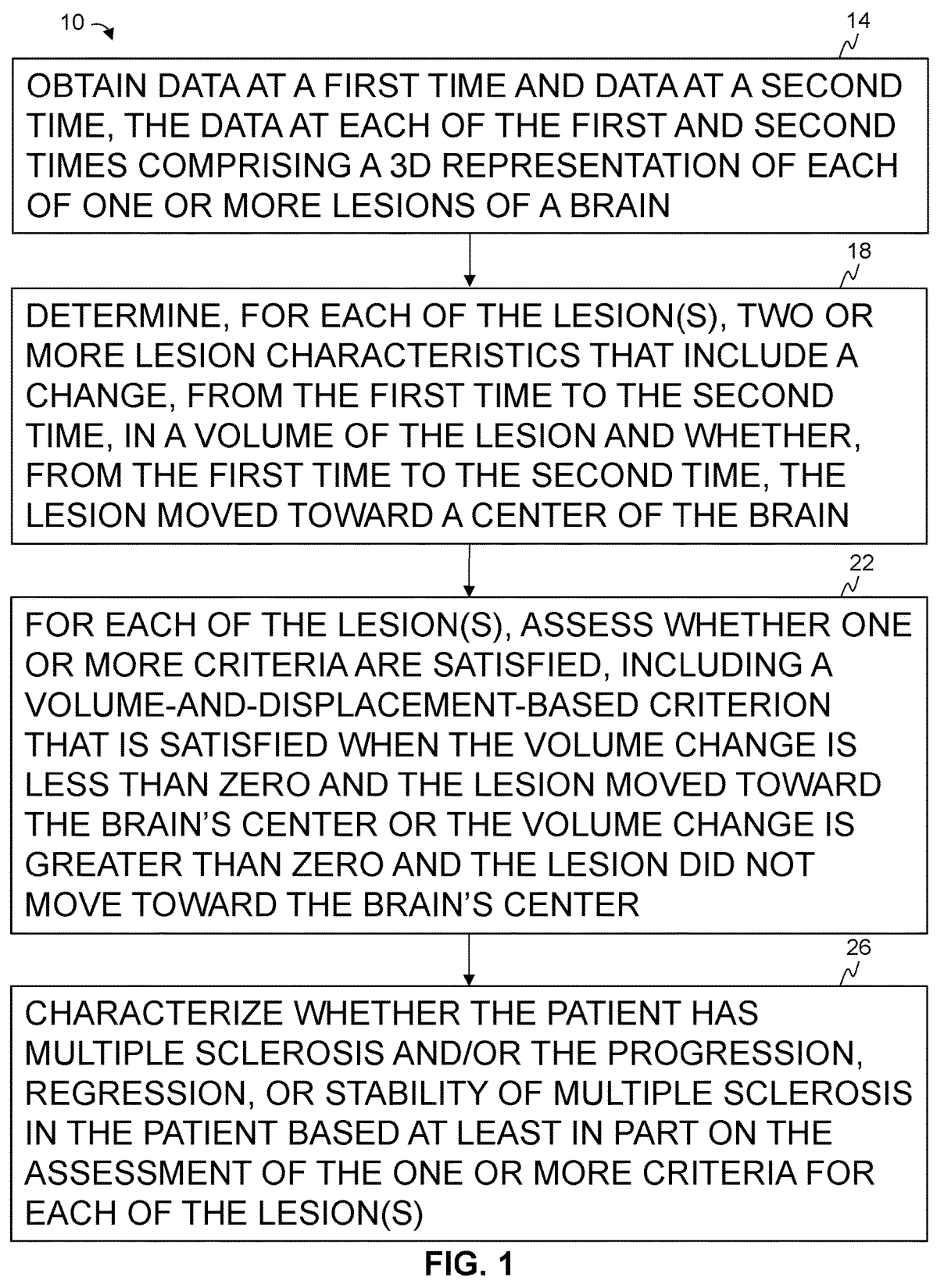

10

14

OBTAIN DATA AT A FIRST TIME AND DATA AT A SECOND TIME, THE DATA AT EACH OF THE FIRST AND SECOND TIMES COMPRISING A 3D REPRESENTATION OF EACH OF ONE OR MORE LESIONS OF A BRAIN

18

DETERMINE, FOR EACH OF THE LESION(S), TWO OR MORE LESION CHARACTERISTICS THAT INCLUDE A CHANGE, FROM THE FIRST TIME TO THE SECOND TIME, IN A VOLUME OF THE LESION AND WHETHER, FROM THE FIRST TIME TO THE SECOND TIME, THE LESION MOVED TOWARD A CENTER OF THE BRAIN

22

FOR EACH OF THE LESION(S), ASSESS WHETHER ONE OR MORE CRITERIA ARE SATISFIED, INCLUDING A VOLUME-AND-DISPLACEMENT-BASED CRITERION THAT IS SATISFIED WHEN THE VOLUME CHANGE IS LESS THAN ZERO AND THE LESION MOVED TOWARD THE BRAIN'S CENTER OR THE VOLUME CHANGE IS GREATER THAN ZERO AND THE LESION DID NOT MOVE TOWARD THE BRAIN'S CENTER

26

CHARACTERIZE WHETHER THE PATIENT HAS MULTIPLE SCLEROSIS AND/OR THE PROGRESSION, REGRESSION, OR STABILITY OF MULTIPLE SCLEROSIS IN THE PATIENT BASED AT LEAST IN PART ON THE ASSESSMENT OF THE ONE OR MORE CRITERIA FOR EACH OF THE LESION(S)

FIG. 1

30
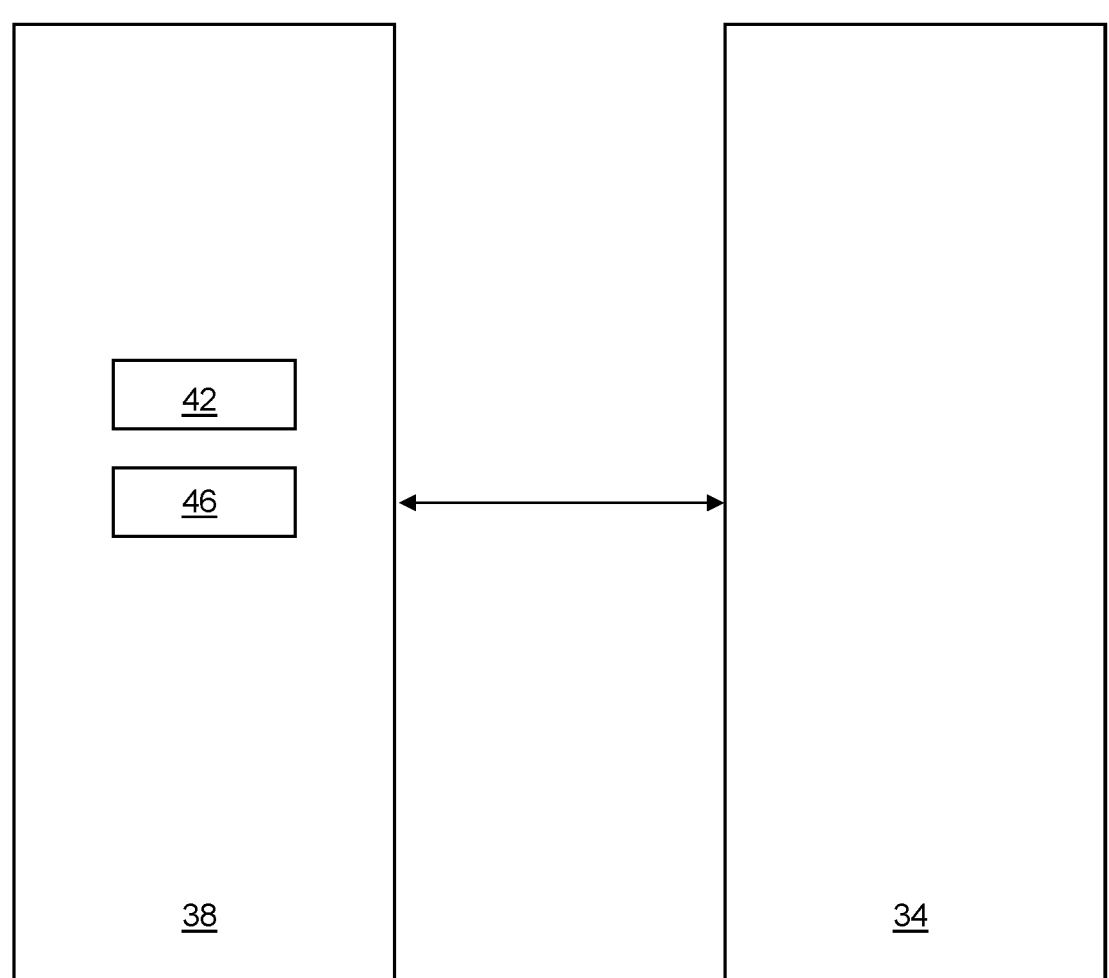
FIG. 2

METHODS AND SYSTEMS FOR ANALYZING BRAIN LESIONS FOR THE DIAGNOSIS OF MULTIPLE SCLEROSIS

This application is a national phase under 35 U.S.C. § 371 of International Application No. PCT/US2022/071023, filed Mar. 8, 2022, which claims the benefit of priority of U.S. Provisional Patent Application No. 63/158,142, filed Mar. 8, 2021, the entire contents of each of which are hereby incorporated by reference in their entireties.

FIELD OF INVENTION

The present invention relates generally to diagnosing and assessing the progression of multiple sclerosis in patients based on the analysis of brain lesions.

BACKGROUND

Multiple sclerosis (MS) is a chronic autoimmune disorder of the central nervous system that results in myelin and axonal injury and subsequent neurodegeneration. The diagnosis of MS is based on both clinical and radiological assessments of damage disseminated in both time and space. This may include a radiological assessment of whether a requisite number of lesions in the periventricular, juxtacortical, infratentorial, and spinal cord regions have a specific character (e.g., size, shape, and morphology) and spatial distribution patterns indicative of MS. The effective application of the existing dissemination in space criteria may be hindered by the highly sensitive nature of magnetic resonance imaging (MRI) technology, the heterogeneity of lesions resulting from a variety of medical conditions, concomitant radiological features resulting from age-related changes and disease, and the lack of additional radiological characteristics beyond two-dimensional (2D) descriptions.

Currently, MS diagnosis is typically performed using 2D MRI images. The implementation of certain imaging metrics, including the use of quantitative phase imaging, has improved lesion specificity. This may highlight the presence of central vasculature within lesions and distinct peripheral rings, suggesting the presence of iron within macrophages. The use of fluid-attenuated inversion recovery (FLAIR) MRI at 3 Tesla (T) and T2-weighted and susceptibility weighted imaging (SWI) at 7 T in larger patient groups has also been utilized to better characterize MS from non-MS lesions. However, this technique has been limited by the lack of appreciation of the central vessel in all orthogonal planes of view and the abundance of vessels intersecting lesions within the supratentorial region. Beyond these efforts, peripheral regions of hypointensity, presumed to be related to the presence of iron within macrophages, have also been described in MS patients.

With these shortcomings, focal lesions resulting from other diseases—such as cerebral small vessel disease (SVD)—may often be misinterpreted as MS lesions, resulting in the misclassification of patients. Accordingly, there is a need in the art for assessments that can more accurately determine whether a patient has MS.

SUMMARY

Some of the present methods and systems address this need in the art through the assessment of a displacement and change in volume of one or more lesions over time, which can be determined from 3-dimensional (3D) MRI images of a patient's brain. A lesion can be characterized as an MS lesion when (1) the lesion's volume decreases and a centroid of the lesion moves toward a center of the brain or (2) when the lesion's volume increases and the lesion's centroid moves away from the brain. An SVD lesion may be less likely to exhibit such a relationship between a change in volume and direction of displacement. Accordingly, this volume-and-displacement-based criterion can facilitate accurate differentiation between MS and non-MS (e.g., SVD) lesions, particularly when assessed using T2-weighted 3D MRI images.

To further facilitate accurate lesion characterization, one or more other criteria can be assessed as well. For example, T1-weighted 3D MRI images can be captured in addition to T2-weighted 3D MRI images; when the T2-weighted 3D MRI images and T1-weighted 3D MRI images each indicate a lesion volume increase, the lesion can be characterized as an MS lesion. As another example, a rate of displacement of the lesion's centroid can be assessed. An MS lesion may tend to exhibit a larger displacement than an SVD lesion, and a lesion can thus be characterized as an MS lesion if a magnitude of the rate of displacement is greater than a threshold rate of displacement, such as 0.16 mm per year. Assessing the above criteria for each of one or more lesions of a brain can yield a more accurate diagnosis of MS compared to conventional techniques.

Some of the present methods of analyzing one or more lesions of a brain of a patient comprise, for each of the lesion(s), from data taken at a first time and data taken at a second time that is after the first time, determining two or more lesion characteristics. Some of the present systems for analyzing one or more lesions of a brain of a patient comprise one or more processors configured to, for each of the lesion(s), from data taken at a first time and data taken at a second time that is after the first time, determine two or more lesion characteristics. The time elapsed between the first and second times, in some embodiments, is between 6 months and 4 years. In some embodiments, the two or more lesion characteristics include a change, from the first time to the second time, in a volume of the lesion and whether, from the first time to the second time, the lesion moved toward a center of the brain. In some embodiments, determining whether the lesion moved toward the center of the brain comprises—or the processor(s) are configured to determine whether the lesion moved toward the center of the brain by—calculating a dot product between first and second vectors, wherein the first vector extends from a centroid of the lesion at the first time to a centroid of the lesion at the second time and the second vector extends from the centroid of the lesion at the second time to the center of the brain, and if the dot product is greater than zero, determining that the lesion moved toward the center of the brain, and if the dot product is less than zero, determining that the lesion did not move toward the center of the brain. In some embodiments, the calculating comprises dividing the dot product by the magnitude of the second vector. The lesion characteristics, in some embodiments, further include a rate of displacement of a centroid of the lesion from the first time to the second time.

Some methods comprise, for each of the lesion(s), assessing whether one or more, optionally two or more, criteria are satisfied and, in some systems, the processor(s) are configured to, for each of the lesion(s), assess whether one or more, optionally two or more, criteria are satisfied. In some embodiments, the one or more criteria include a volume-and-displacement-based criterion that is satisfied when from the determination of the lesion characteristics the change in the volume of the lesion is less than zero and the lesion moved toward the center of the brain or the change in the volume of the lesion is greater than zero and the lesion did not move toward the center of the brain. In some embodiments, the one or more criteria include a displacement-rate-based criterion that is satisfied when from the determination of lesion characteristics a magnitude of the rate of displacement is greater than a threshold rate of displacement. The threshold rate of displacement, in some embodiments, is greater than or equal to 0.16 mm per year.

Some systems comprise an MRI device. In some embodiments, that data taken at the first time and the data taken at the second time each includes one or more magnetic resonance imaging (MRI) images of the brain of the patient that comprise a 3D representation of each of the lesion(s). For each of the lesion(s), in some embodiments, the change in the volume of the lesion and whether the lesion moved toward the center of the brain are determined from—or the processor(s) are configured to determine the change in the volume of the lesion and whether the lesion moved toward the center of the brain from—the 3D representations of the lesion. In some embodiments, for each of the data taken at the first time and the data taken at the second time, the MRI image(s) each is a T2-weighted MRI image. In some embodiments, the data taken at the first time and the data taken at the second time each further includes one or more T1-weighted MRI images that comprise a 3D representation of each of the lesion(s). In some of such embodiments, for each of the lesion(s), the change in the volume of the lesion is a first change in the volume of the lesion, the lesion characteristics include a second change, from the first time to the second time, in a volume of the lesion, the second change in the volume of the lesion determined from the 3D representations of the lesion from the T1-weighted MRI images, and the one or more criteria comprise two or more criteria that further include a volume-based criterion that is satisfied when each of the first and second changes in the volume of the lesion is greater than zero.

Some methods comprise characterizing whether the patient has multiple sclerosis and/or the progression, regression, or stability of multiple sclerosis in the patient based at least in part on the assessment of the one or more criteria for each of the lesion(s). In some methods, the characterizing comprises determining that the patient has multiple sclerosis and/or that multiple sclerosis is progressing in the patient when at least one of the one or more criteria is satisfied for at least one—optionally for at least a majority—of the lesion(s). In some systems, the processor(s) are configured to characterize whether the patient has multiple sclerosis and/or the progression, regression, or stability of multiple sclerosis in the patient based at least in part on the assessment of the one or more criteria for each of the lesion(s). In some systems, the processor(s) are configured to determine that the patient has multiple sclerosis and/or that multiple sclerosis is progressing in the patient when at least one of the one or more criteria is satisfied for at least one—optionally for at least a majority—of the lesion(s).

The terms "a" and "an" are defined as one or more unless this disclosure explicitly requires otherwise. The terms "substantially" and "about" each is defined as largely but not necessarily wholly what is specified—and includes what is specified; e.g., substantially or about 90 degrees includes 90 degrees and substantially or about parallel includes parallel—as understood by a person of ordinary skill in the art. In any disclosed embodiment, the terms "substantially" and "about" may each be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, a system that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the systems and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a system or component thereof that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 1 illustrates some of the present methods of analyzing one or more lesions of a brain using 3D MRI images.

FIG. 2 is a schematic of a system that can be used to perform some of the present methods.

FIG. 5 also shows superimposed 3D representations of a lesion of the brain from the 3D MRI images (labelled E), including representations of the lesion at the first time (solid pink polyhedron, from the T1-weighted image, and yellow mesh polyhedron, from the T2-weighted image) and at the second time (solid green polyhedron, from the T1-weighted image, and blue mesh polyhedron, from the T2-weighted image). The patient was a 27-year-old white woman with relapsing remitting MS, and the second time was 4-years after the first time.

DETAILED DESCRIPTION

Referring to FIGS. 1 and 2, shown is an illustrative method 10 for analyzing one or more brain lesions of a patient and a system 30 configured to perform method 10. While some of the present methods are described with reference to system 30, system 30 is not limiting on those methods, which can be performed with any suitable system.

Some of the present methods include a step 14 of obtaining data at a first time and data at a second time that is after the first time, the data at each of the first and second times including a 3D representation (e.g., 56a and 56b) of each of one or more—optionally, a plurality of—lesions (e.g., 54) of a patient's brain. For example, the data taken at the first time and the data taken at the second time can each include a 3D MRI image (e.g., a T1-weighted or a T2-weighted 3D MRI image) of the brain taken with an MRI device (e.g., 34) of system 30. For each of the 3D MRI images, the 3D representation of each of the lesion(s) can be segmented from the image for analysis. The data taken at the first and second times can also each include a plurality of 2D MRI images that together can form a 3D representation of the brain (e.g., by stitching the images together). As described in further detail below, the data taken at each of the first and second times can include multiple MRI image types—such as both T1-weighted MRI image(s) and T2-weighted MRI image(s)—that each comprises a 3D representation of each of the lesion(s), which can allow one or more lesion criteria that compare the T1-weighted and T2-weighted data to be assessed to facilitate an MS diagnosis. Any suitable time can be elapsed between the first and second times; for example, the time elapsed between the first and second times can be greater than or equal to any one of, or between any two of, 3 months, 4 months, 5 months, 6 months, 1 year, 2 years, 3 years, or 4 years (e.g., between 6 months and 4 years).

Figure 3A:
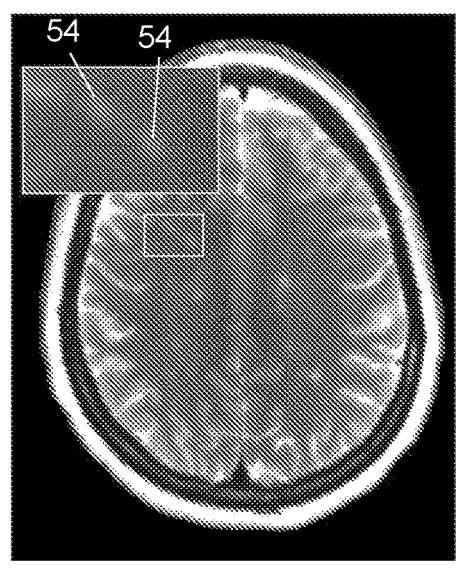
FIGS. 3A and 3B are 3D MRI axial T2-weighted images of a brain of a 22-year-old African American woman with relapsing remitting MS at first and second times, respectively, the second time 2-years after the first time.
Figure 3B:
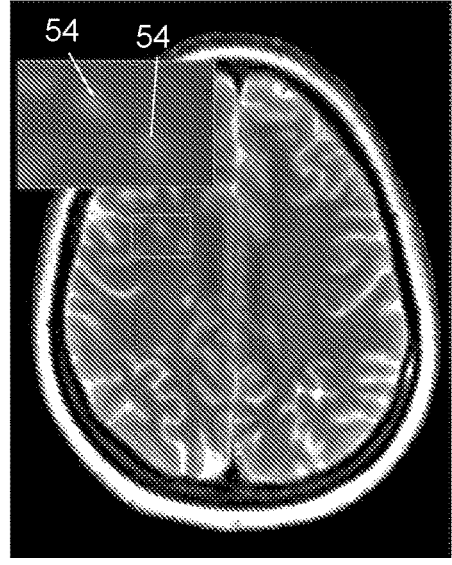

To obtain the 3D representations of each of the lesion(s) from the MRI images, system 30 can include a processing device (e.g., 38) having one or more processors configured to receive each of those images and a segmentation application (e.g., 42) by which the processor(s) can segment the 3D MRI image (or stitched-together 2D MRI images) into one or more regions of interest (ROIs) that can each correspond to one of the brain lesion(s). An illustrative segmentation application is OsiriX from Pixmeo SARL of Geneva, Switzerland. The processing device can be a part of a computer system including standard components such as a hard drive, monitor, printer, keyboard, and mouse, and/or the like that may enable a user to interact with the processing device. As illustrated in the MRI images in FIGS. 3A and 3B, non-contrast MRI sequences effectively allow for the identification of brain lesion(s), which can exhibit a higher intensity than other portions of the brain in the image and thus can be identified as ROIs. In other embodiments, however, the 3D representations can be obtained from contrast-enhanced MRI imaging. To facilitate segmentation, before the MRI device images the patient's brain, a contrast agent (e.g., a paramagnetic agent such as a gadolinium-based contrast agent, an agent including a dye/pigment, and/or the like) can be administered to the patient such that the contrast agent enters the patient's bloodstream and travels to the brain. Because the blood-brain barrier at brain lesions may be compromised, a higher concentration of the contrast agent may be present at the brain lesion(s) compared to other regions in the brain.

Figure 3C:
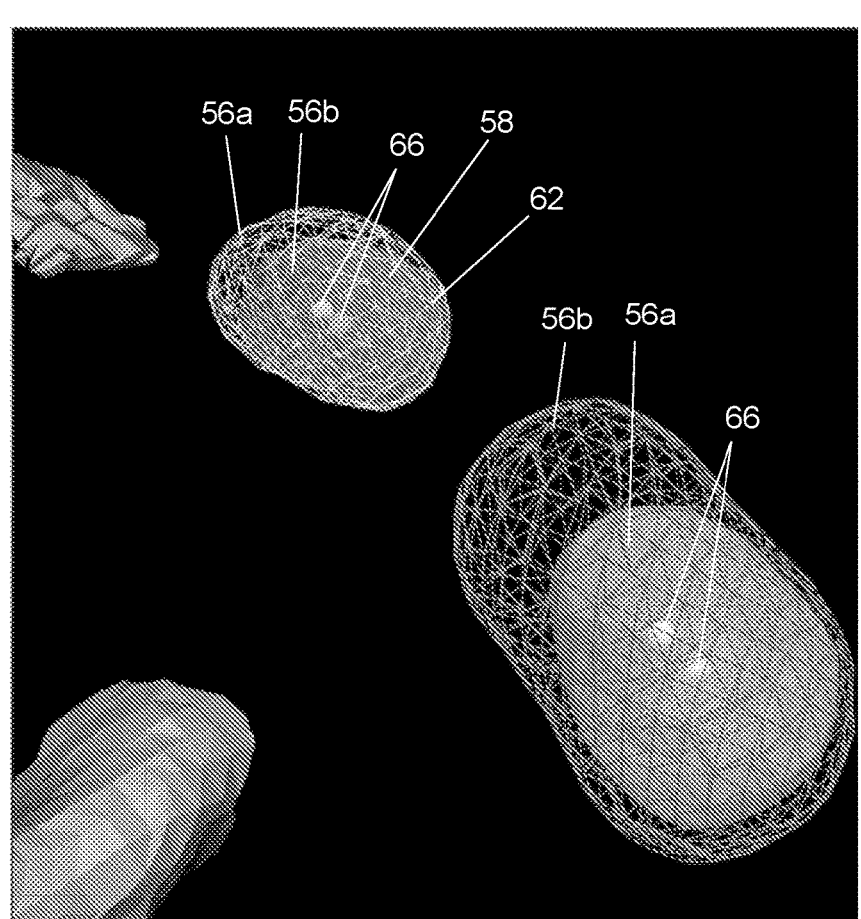
FIG. 3C shows 3D representations of two lesions from the FIGS. 3A and 3B images, wherein from the first time to the second time, the first lesion decreased in volume (teal mesh polyhedron shrinking to a solid red polyhedron) and had a centroid that moved toward the center of the scan, and the second lesion increased in volume (solid teal polyhedron expanding to a red mesh polyhedron) and had a centroid that moved away from the center of the scan.

Each of the 3D representations of a lesion can comprise data that represents the geometry of the lesion (e.g., from which the volume thereof can be calculated) and, optionally, the lesion's position in the brain. For example, FIG. 3C depicts, for each of two brain lesions, orthographic projections of a first 3D representation (e.g., 56a) of the lesion at the first time and a second 3D representation (e.g., 56b) of the lesion at the second time superimposed on one another. The 3D representations can each represent the lesion as a polyhedron whose surface is defined by a plurality of polygons (e.g., triangles) (e.g., 58) and include data regarding the position of the polygons' vertices (e.g., 62) in 3D coordinates (e.g., 3D Cartesian coordinates) and/or the polygons' unit normals. As an illustration, the first and second 3D representations can each be a stereolithography (.stl) file representing the surface geometry of the lesion at the first and second times, respectively. In other embodiments, however, the first and second 3D representations can include any suitable data representing the geometry of the lesion.

Some of the present methods include a step 18 of, from the data taken at the first and second times, determining two or more characteristics of each of the lesion(s). The lesion characteristics can include: (1) a change, from the first time to the second time, in a volume of the lesion, (2) whether, from the first time to the second time, the lesion moved toward a center of the brain, and/or (3) a rate of displacement of a centroid of the lesion from the first time to the second time. To do so, the processing system can include a 3D imaging application (e.g., 46) by which the processor(s) can calculate the lesion characteristics from the data taken at the first and second times (e.g., at least in part from the 3D representations of each of the lesions at the first and second times).

To illustrate, when the first and second 3D representations of a lesion each represents the lesion as a polyhedron whose surface is defined by a plurality of triangles (e.g., when each is a stereolithography file), the lesion volume can be calculated by (1) for each of the triangles, calculating the signed volume of a tetrahedron having a base defined by the triangle and a vertex at the origin and (2) summing the signed volumes to determine the total lesion volume. The change in the lesion volume can be determined by subtracting the volume calculated from the first 3D representation from the volume calculated from the second 3D representation. In other embodiments, however, the volume change can be determined in any suitable manner.

Figure 4:
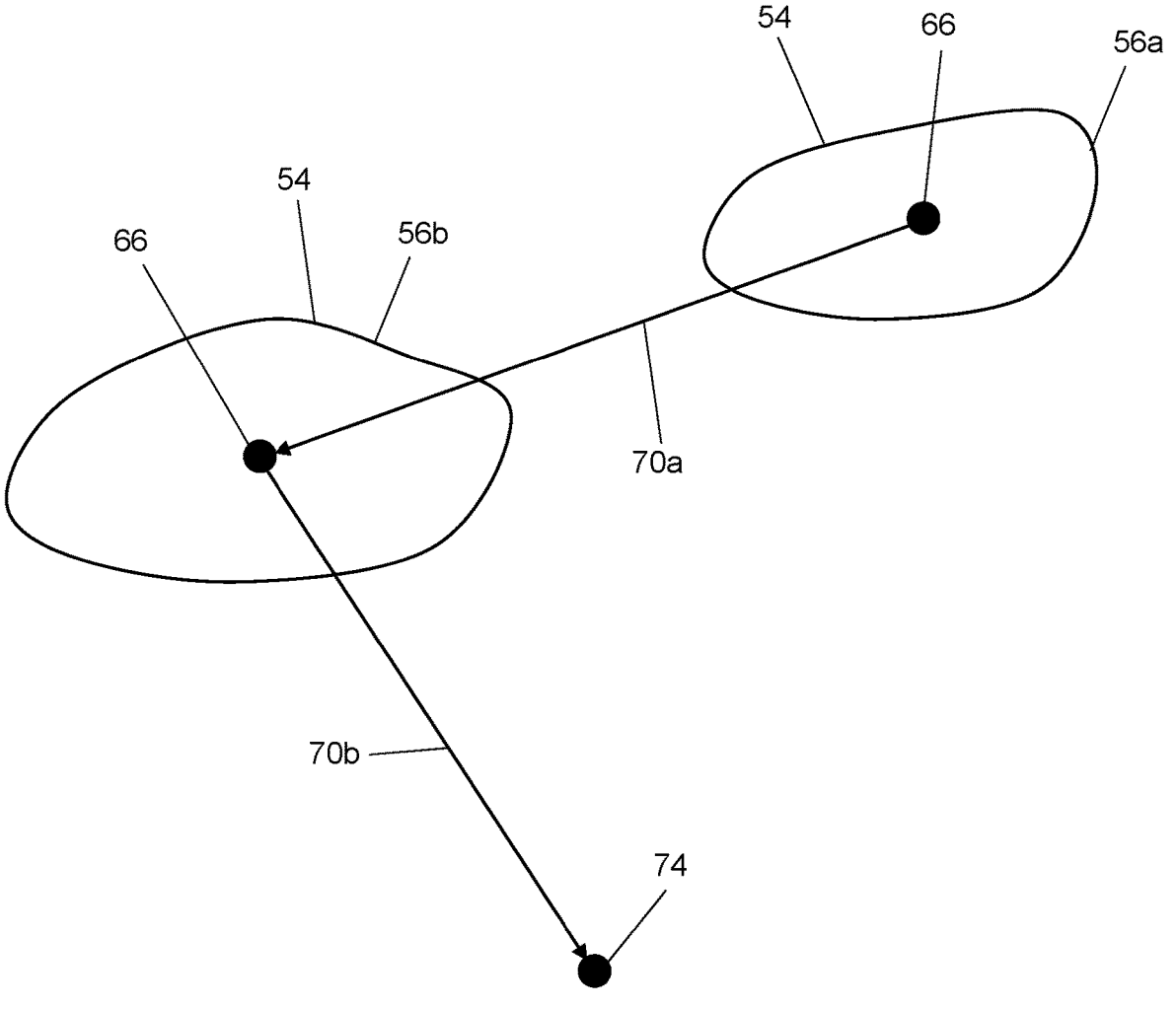
FIG. 4 is a schematic illustrating a lesion at first and second times, with a first vector extending from the lesion's centroid at the first time to the lesion's centroid at the second time and a second vector extending from the lesion's centroid at the second time to a center of the brain. A dot product between the first and second vectors can be calculated to characterize whether the lesion's centroid moved toward the center of the brain.

Referring to FIG. 4, to determine whether a lesion moved toward a center (e.g., 74) of the brain, the position of the lesion's centroid (e.g., 66) at the first time and at the second time can be determined (e.g., from the first and second 3D representations of the lesion). As shown, first and second vectors (e.g., 70a and 70b) can be determined, wherein the first vector extends from the lesion's centroid at the first time to the lesion's centroid at the second time and the second vector extends from the lesion's centroid at the second time to the center of the brain. The position of the center of the brain (e.g., the center of the scan) can be calculated by determining an array of vertices that bound the image of the brain and taking the average thereof.

A dot product between the first and second vectors can be calculated, and optionally can be divided by the magnitude of the second vector (e.g., to convert the second vector to a unit vector) to mitigate the impact of the second vector's length on the dot product. If the dot product is greater than zero, it can be determined that the lesion moved toward the center of the brain, and if the dot product is less than (or equal to) zero, it can be determined that the lesion did not move toward the center of the brain. In other embodiments, however, a different calculation can be performed to determine if the lesion moved toward the center of the brain. For example, the second vector used in the above-described dot product calculation can instead extend from the lesion's centroid at the first time to the center of the brain. Alternatively, while yielding less accurate results for the below-described MS diagnostics than the dot product approach, determining whether the lesion moved toward the center of the brain can be performed by comparing the distance between the lesion's centroid and the center of the brain at the first time and the distance between the lesion's centroid and the center of the brain at the second time.

The rate of displacement of a lesion's centroid can be assessed by calculating a magnitude of the lesion's displacement from the first time to the second time (e.g., the magnitude of the first vector) and dividing the magnitude by the amount of time elapsed between the first and second times.

Some methods comprise a step 22 of assessing, for each of the lesion(s), whether one or more criteria are satisfied, and a step 26 of characterizing whether the patient has MS and/or the progression, regression, or stability of MS in the patient based at least in part on the assessment of the one or more criteria. The processor(s) can be configured to perform the assessment of the one or more criteria and/or characterization of the presence and/or progression, regression, or stability of MS in the patient. The one or more criteria may permit MS lesions to be distinguished from, for example, SVD lesions; a patient can be diagnosed as having MS and/or MS can be characterized as progressing or not in remission when at least one of the one or more criteria is satisfied for at least one (e.g., at least a majority) of the lesion(s).

The one or more criteria can include a volume-and-displacement-based criterion that is satisfied when it is determined that (1) the lesion's volume decreased (e.g., the change in volume is less than zero) and the lesion moved toward the center of the brain, or (2) the lesion's volume increased (e.g., the change in volume is greater than zero) and the lesion did not move toward the center of the brain. A lesion whose volume decreases while moving toward the brain's center or whose volume increases while moving away from the brain's center can have a greater likelihood of being an MS lesion than an SVD lesion, and thus satisfaction of the volume-and-displacement-based criterion may weigh in favor of a determination that the lesion is an MS lesion. Use of the volume-and-displacement-based criterion may facilitate more accurate diagnostics, particularly when T2-weighted MRI images taken at the first and second times are used for the assessment.

Figure 6A:
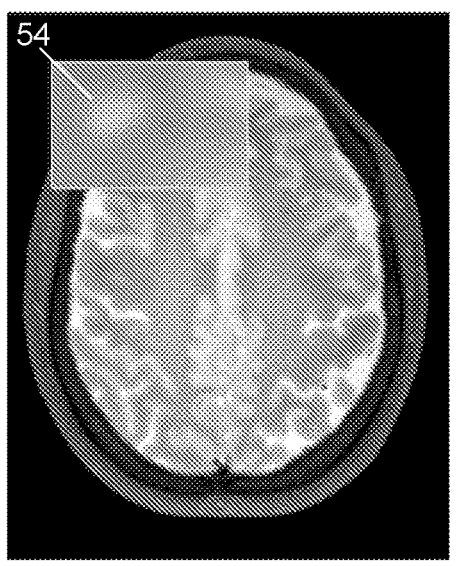
FIGS. 6A and 6B are 3D MRI axial T2-weighted images of a brain of a 42-year-old Hispanic woman with SVD taken at first and second times, respectively, the second time 4-years after the first time.
Figure 6B:
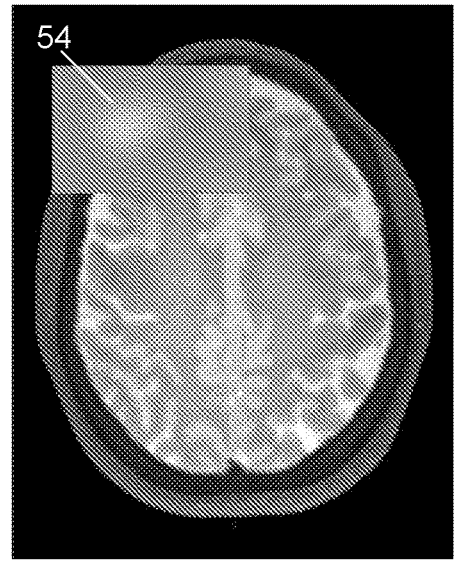
Figure 6C:
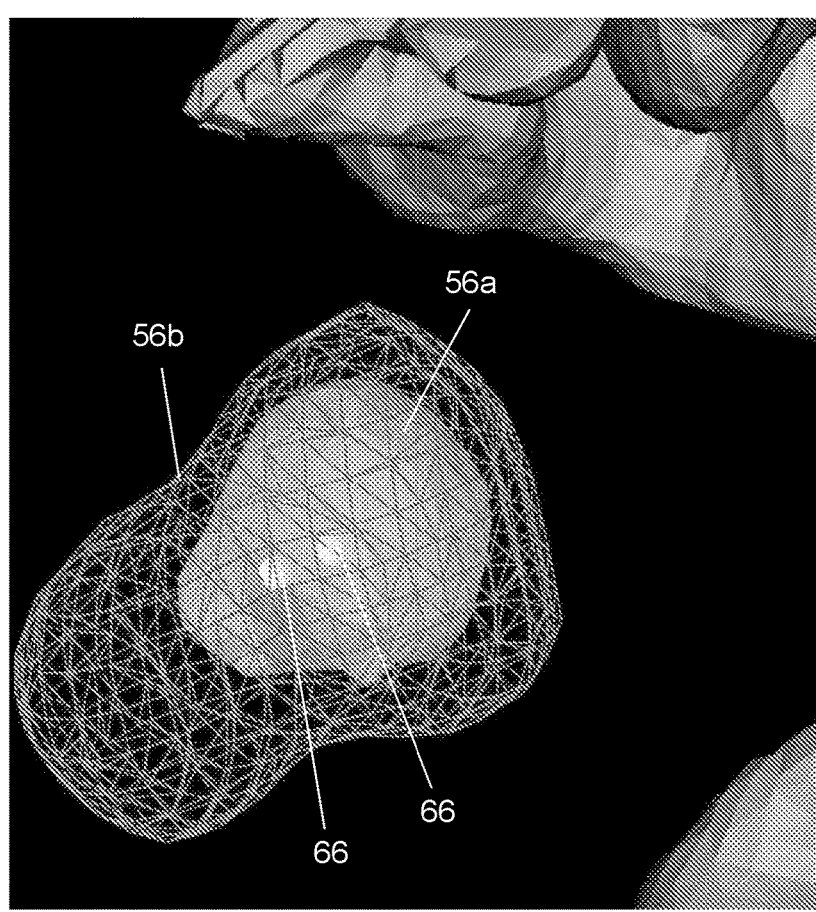
FIG. 6C shows 3D representations of the lesion from the FIGS. 6A and 6B images, wherein from the first time to the second time the lesion volume increase (solid teal polyhedron expanding to a red mesh polyhedron) and the lesion's centroid moved toward the center of the scan.

For example, FIG. 3C shows 3D representations of two lesions of an MS patient that each satisfies the volume-and-displacement based criterion, the 3D representations obtained from T2-weighted 3D MRI images. As shown, the first, smaller lesion's volume decreases (illustrated as the teal mesh polyhedron contracting to a solid red polyhedron) and its centroid moves from the teal point to the red point toward the center of the brain (e.g., away from the brain's grey matter, illustrated in orange). The second, larger lesion's volume increases (illustrated as the teal solid polyhedron expanding to a mesh red polyhedron) and its centroid moves from the yellow point to the white point away from the center of the brain and toward the brain's grey matter. Referring to FIGS. 6A-6C, by contrast, shown are T2-weighted 3D MRI images of a brain of an SVD patient taken at first and second times (FIGS. 6A and 6B) and 3D representations of a lesion thereof (FIG. 6C). The SVD patient's lesion increases in volume (illustrated as the solid teal polyhedron expanding to the red mesh polyhedron) and its centroid moves from the yellow point to the white point toward the center of the brain (e.g., away from the brain's grey matter, illustrated in orange). The illustrated SVD lesion thus does not satisfy the volume-and-displacement based criterion.

The one or more criteria can also include a volume-based criterion. As noted above, the data obtained at each of the first and second times can include both T1-weighted MRI image(s) of the brain and a T2-weighted MRI image(s) of the brain, each comprising a 3D representation of each of the lesion(s) (e.g., with lesion(s) of the T1-weighted MRI each identified from a hyperintensity in the image and lesion(s) of the T2-weighted MRI each identified from a hypointensity in the image). In such embodiments, the measured lesion characteristics can include two changes in the lesion's volume from the first time to the second time: a first change in volume determined based on the T2-weighted MRI images, and a second change in volume determined based on the T1-weighted MRI images. The volume-based criterion can be satisfied when the first and second changes in volume each is greater than zero. An indication from both T1-weighted and T2-weighted MRI images that a lesion's volume increased may weigh in favor of a determination that the lesion is an MS lesion.

Figure 5:
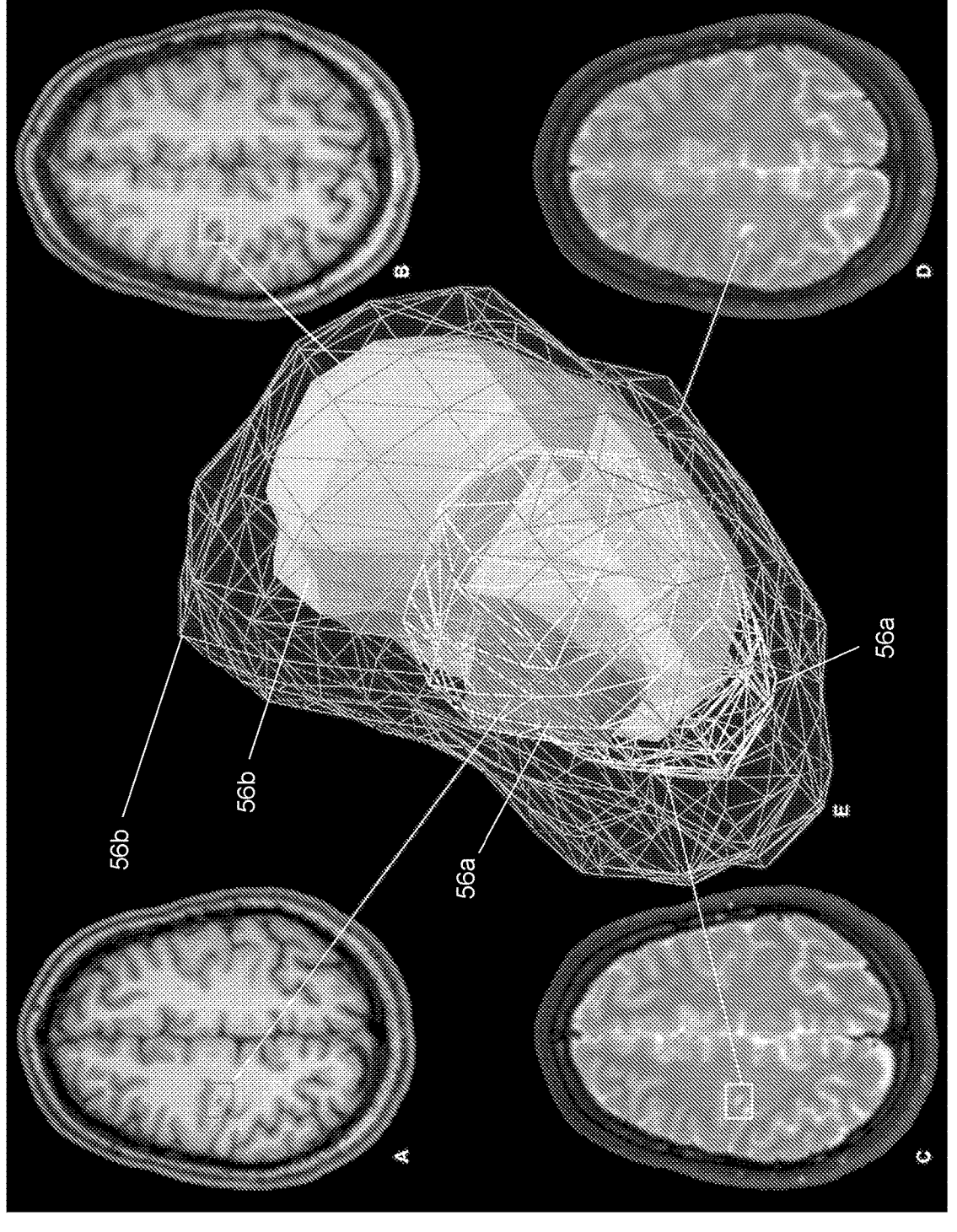
FIG. 5 shows 3D MRI axial T1-weighted images of a patient's brain taken at first and second times (labelled A and B, respectively) and 3D MRI axial T2-weighted images of a patient's brain taken at the first and second times (labelled C and D, respectively).

To illustrate, FIG. 5 shows 3D representations of a lesion of an MS patient that satisfies the volume-based criterion. As shown, the data from which the 3D representations are derived includes T1-weighted 3D MRI images taken at the first and second times (labelled A and B, respectively) and T2-weighted 3D MRI images taken at the first and second times (labelled C and D, respectively). The lesion's volume increased both as determined from the T1-weighted 3D MRI images (illustrated as the solid pink polyhedron expanding to the solid green polyhedron) and as determined from the T2-weighted 3D MRI images (illustrated as a yellow mesh polyhedron expanding to a blue mesh polyhedron). The lesion thus satisfies the volume-based criterion, consistent with the lesion being one of an MS patient.

The one or more criteria can also comprise a displacement-rate-based criterion that is satisfied when from the determination of lesion characteristics a magnitude of the rate of displacement is greater than a threshold rate of displacement. The threshold rate of displacement can be greater than or equal to any one of, or between any two of, 0.13, 0.14, 0.15, 0.16, 0.17, 0.18, 0.19, 0.20, 0.21, 0.22, 0.23, 0.24, or 0.25 millimeters (mm) per year (e.g., at least 0.16 mm per year). MS lesions may be more likely than SVD lesions to experience displacements at a rate that is higher than such thresholds. Satisfaction of the displacement-rate-based criterion may thus weigh in favor of a determination that the lesion is an MS lesion.

Due to the heterogeneity of MS lesions, a lesion need not satisfy all criteria to be indicative of the presence and/or progression of MS (e.g., satisfaction of at least one of the one or more criteria may at least in part support a finding that the patient has MS and/or that MS is progressing). When the brain includes multiple lesions, referencing each of those lesions to determine the geometric characteristics thereof and assess the one or more criteria based on the calculated characteristics may facilitate a more accurate characterization of the presence of MS in a patient despite this heterogeneity. With the presence of more lesions satisfying more of the above-described criteria, it may be more likely that the patient has MS and/or that MS is progressing in the patient. For example, it can be determined that the patient has MS and/or that MS is progressing in the patient when for at least a majority of the lesions, such as greater than or equal to any one of or between any two of 50%, 60%, 70%, 80%, or 90% (e.g., at least 55%) of the lesions, at least one of the one or more criteria (e.g., the volume-and-displacement-based criterion, volume-based-criterion, and/or displacement-rate-based criterion) is satisfied.

Characterizing whether the patient has MS can include a determination that the patient has MS (e.g., if at least one of the criteria is satisfied for at least one, optionally a majority, of the lesion(s)) and/or another disease, such as SVD. It can also include a determination of the patient's risk of having MS and/or another disease (e.g., SVD). Characterizing the progression, regression, or stability of MS in the patient can include a determination of whether—for a patient having MS—MS is progressing or is not progressing (e.g., is stable or in remission). For example, some methods can be performed to assess the efficacy of a treatment; in such methods, the treatment (e.g., a medication) can be administered to the patient (e.g., between the first and second times), where a determination that MS is in remission may indicate that the treatment is effective while a determination that MS is not in remission may indicate that it is not.

The use of 3D—rather than 2D—representations of each of the lesion(s) taken at different points in time may promote the accurate diagnosis and assessment of MS. The time-based geometric characteristics that may vary between MS and SVD lesions (e.g., criteria based on the change in volume, whether the lesion moved toward the center of the brain, and/or the magnitude of the rate of displacement of the lesion) may not be apparent in 2D representations of a lesion, even for representations obtained from high-resolution MRI images. However, these characteristics may be detectable from 3D representations of a lesion such that they can be quantified and assessed. Because MS and SVD lesions may exhibit different changes in at least some of these geometric characteristics over time, the assessment based on 3D representations may permit more specific and accurate diagnosis of a patient.

EXAMPLES

Aspects of the present invention will be described in greater detail by way of specific examples. The follow examples are offered for illustrative purposes only and are not intended to limit the invention in any manner. Those of skill in the art will readily recognize a variety of noncritical parameters that can be changed or modified to yield essentially the same results.

Example 1

Brain lesions of 47 patients were analyzed using 3D MRI. The patients were placed in two groups: (1) patients with a confirmed MS diagnosis based on established criteria and results from supporting para-clinical studies (i.e., cerebrospinal fluid profiles, electrophysiological data, and/or serological results) to the exclusion of other disease states, and (2) patients with a confirmed SVD diagnosis centered on the lack of clinical data related to symptoms consistent with CNS demyelination, results from supporting para-clinical studies, and the observation of brain anomalies atypical for CNS demyelination based on the observed radiological features and formal imaging interpretations performed by a board-certified neuroradiologist and clinical impressions from an MS specialist, to the exclusion of a better medical reason for the observed imaging data. Of the 47 patients, 35 had a confirmed MS diagnosis (Group 1) and 12 had a confirmed SVD diagnosis (Group 2). In total 420 lesions were analyzed, with 280 lesions being from the MS patients and 140 lesions being from the SVD patients.

Imaging was performed with a 3T MRI scanner from Philips Medical Systems, Cleveland OH, using a 32-channel phased array coil for reception and body coil for transmission. Each MRI study included scout localizers, 3D high-resolution inversion recovery spoiled gradient-echo T1-weighted isotropic ($1.1 \times 1.1 \times 1.1$ mm$^3$, TE/TR/TI=3.7/8.1/864 ms, flip angle 12 degrees, $256 \times 220 \times 170$ mm$^3$ FOV, number of excitations (NEX)=1,170 slices, duration: 4:11 min), 3D fluid-attenuated inversion recovery (FLAIR) ($1.1 \times 1.1 \times 1.1$ mm$^3$, TE/TR/TI=350/4800/1600 ms, flip angle 90 degrees, $250 \times 250 \times 180$ mm$^3$ FOV, NEX=1,163 slices, duration: 5:02 min), and 3D T2-weighted sequence acquired in sagittal plane ($1.0 \times 1.0 \times 1.0$ mm$^3$, TE/TR/TI=229/2500/1600 ms, flip angle 90 degrees, $250 \times 250 \times 180$ mm$^3$ FOV, NEX=1, 164 slices, duration: 4:33 min). For each patient, MRI was performed at two points in time.

Lesions were segmented from the MRI images without knowledge of the patients' clinical histories, current or past treatments, or disease durations. MRI registration was initially performed based on anatomical positioning and intensity using an in-house software package (Med-IP, which was used in prior studies, such as in Sivakolundu et al., BOLD signal within and around white matter lesions distinguishes multiple sclerosis and non-specific white matter disease: a three dimensional approach, J. Neurol. 2020) and were aligned using the Insight Toolkit (version 5.1.1, from Kitware, Clifton Park, NY), and multi-resolution rigid registration was performed with the Mattes Mutual Information Metric. To ensure proper intensity alignment, histogram matching of intensities involving regions of interest through linear transforms and ordered correspondence on a set of match points computed from the quantiles of each histogram were performed. The selection of focal brain lesions with an area greater than 3 mm$^2$ within the supratentorial region were verified from simultaneously-viewed 3D high-resolution FLAIR and T2-weighted sequences. The segmented lesions were saved as region of interest files for analysis. Segmentation of T1-hypointensities from SVD patients were not performed due to technical challenges in effectively segmenting lesions with lower volumes.

Visualization Toolkit (VTK) (version 3.7.5, from Kitware, Clifton Park, NY) was used for the visualization and analysis of lesions. The center of the brain (center of the scan) was calculated using an array of points acquired from the bounds of the brain. For each lesion, two vectors were acquired: a first vector extending from the centroid of the lesion at the first time to the centroid of the lesion at the second time and a second vector extending from the centroid of the lesion at the second time to the center of the brain. The dot product between the two vectors was calculated—with the second vector normalized to its length to yield a unit vector—to characterize whether the lesion moved toward the center of the brain, with a negative dot product indicating movement away from the brain's center and a positive dot product indicating movement toward the brain's center. The magnitude of displacement of each of the lesion centroids was also calculated, as was the direction of centroid movement using Cartesian coordinates: a positive x-displacement indicated movement toward the back of the head while a negative x-displacement indicated movement toward the front of the head, a positive y-displacement indicated movement toward the top of the head while a negative y-displacement indicated movement toward the bottom of the head, and a positive z-displacement indicated movement toward the left ear while a negative z-displacement indicated movement toward the right ear. The change in volume of each of the lesions was also determined.

TABLES 1 and 2, below, set forth the clinical data (e.g., patient characteristics) and lesion data (e.g., lesion characteristics calculated during the study) for the MS patients and SVD patients, respectively. As reflected in the tables, T1-hypointensity and T2-hyperintensity lesions were each separated into two groups: lesions whose volume increased and lesions whose volume decreased. Characteristics of patients having both increasing-volume and decreasing-volume lesions were accounted for in both groups. The median values provided in the table are accompanied by the range of values from which the median was determined.

TABLE 1

| | T1-hypointensity | | T2-hyperintensity | |
|---|---|---|---|---|
| Clinical and Lesion Data for MS Patients | Increase in Volume | Decrease in Volume | Increase in Volume | Decrease in Volume |
| Subjects | 29 | 35 | 28 | 33 |
| Lesions | 104 | 176 | 107 | 173 |
| Female (%) | 18 (62.07%) | 22 (62.86%) | 17 (60.71%) | 20 (60.61%) |
| Race (%) | | | | |
| White | 24 (82.76%) | 28 (80%) | 23 (82.14%) | 26 (78.79%) |
| Black | 5 (17.24%) | 6 (17.14%) | 5 (17.86%) | 6 (18.18%) |
| Arabic | 0 (0%) | 1 (2.86%) | 0 (0%) | 1 (3.03%) |
| Hispanic (%) | 4 (13.79%) | 4 (11.43%) | 4 (14.29%) | 3 (9.09%) |
| Median Age (years) | 37.55 (22.61-61.56) | 38.15 (22.61-61.56) | 37.85 (22.61-61.56) | 38.15 (22.61-57.99) |
| Median Disease Duration (years) | 7.38 (0.38-20.99) | 7.38 (0.38-22.61) | 7.18 (0.38-22.61) | 6.99 (0.38-22.61) |
| Median Time Between Scans (years) | 1.88 (0.77-3.99) | 1.68 (0.77-3.99) | 1.67 (0.84-3.83) | 1.85 (0.77-3.99) |
| Median Rate of Change of Surface Area (mm²/year) | 3 (−5.31-44.08) | −6.66 (−97.27-13.34) | 7.05 (−66.02-93.16) | −5.04 (−213.31-40.34) |
| Median Rate of Change of Volume (mm³/year) | 2.77 (−1.73-88.53) | −4.65 (−117.35--0.01) | 8.72 (0.13-98.8) | −5.98 (−341.19-0.01) |
| Lesions Moving Towards Center of Scan (%) | 55 (52.88%) | 93 (52.84%) | 28 (26.17%) | 139 (80.35%) |
| Median Distance Centroid at Time 1 from Center (mm) | | | | |
| X | 10.76 (−46.4-61.5) | 11.6 (−57.99-80.95) | 17.74 (−53.11-74.56) | 8.95 (−45.39-69.56) |
| Y | 37.24 (−57.77-80.65) | 40.93 (−63.13-81.96) | 37.89 (−4.15-84.32) | 46.56 (−17.95-84.16) |
| Z | 24.06 (0.5-75.63) | 23.53 (0.59-86.59) | 25.41 (4.08-50.46) | 23.37 (4.27-52.36) |
| Median Rate of Lesion Centroid Change (mm/year) | | | | |
| X | 0.02 (−0.62-0.73) | 0.03 (−0.6-0.53) | 0.03 (−0.62-0.77) | 0.02 (−1.04-1.48) |
| Y | −0.04 (−0.82-1.14) | −0.05 (−0.62-0.97) | 0.02 (−0.59-1.1) | −0.05 (−1.52-0.46) |
| Z | 0 (−0.97-6.27) | 0 (−0.66-0.48) | 0 (−0.7-0.72) | 0.01 (−0.86-0.67) |
| Median Rate of Lesion Movement Magnitude (mm/year) | 0.31 (0.05-6.41) | 0.31 (0.03-1.02) | 0.2 (0.02-1.52) | 0.19 (0.03-2.12) |

TABLE 2

| Clinical and Lesion Data for SVD Patients | | |
| --- | --- | --- |
| | T2-hyperintensity | |
| | Increase in Volume | Decrease in Volume |
| Subjects | 12 | 12 |
| Lesions | 94 | 46 |
| Female (%) | 12 (100%) | 12 (100%) |
| Race (%) | | |
| White | 12 (100%) | 12 (100%) |
| Black | 0 (0%) | 0 (0%) |
| Arabic | 0 (0%) | 0 (0%) |
| Hispanic (%) | 2 (16.67%) | 2 (16.67%) |
| Median | 54.53 | 54.53 |
| Age (years) | (40.13-66.14) | (40.13-66.14) |
| Median Disease | 10.97 | 10.97 |
| Duration (years) | (0.22-18.26) | (0.22-18.26) |
| Median Time | 2.4 | 2.4 |
| Between | (0.8-3.85) | (0.8-3.85) |
| Scans (years) | | |
| Median Rate of | 3.13 | −2.05 |
| Change of Surface | (−5.18-23.83) | (−79.29-0.38) |
| Area (mm$^2$/year) | | |
| Median Rate of | 3.89 | −2.73 |
| Change of Volume | (0.04-22.06) | (−53.85--0.01) |
| (mm$^3$/year) | | |
| Lesions Moving | 64 (68.09%) | 13 (28.26%) |
| Towards Center | | |
| of Scan (%) | | |
| Median Distance | | |
| Centroid at Time 1 | | |
| from Center (mm) | | |
| X | 12.05 | 7.15 |
| | (−56.77-64.87) | (−42.81-59.36) |
| Y | 44.03 | 48.35 |
| | (−7.3-86.58) | (11.29-78.77) |
| Z | 27.26 | 25.03 |
| | (8.04-52.77) | (9.26-43.29) |
| Median Rate of | | |
| Lesion Centroid | | |
| Change (mm/year) | | |
| X | 0 | 0.03 |
| | (−0.4-0.43) | (−0.12-0.2) |
| Y | −0.01 | 0.01 |
| | (−1.1-0.34) | (−0.26-1.22) |
| Z | 0 | 0 |
| | (−0.33-0.31) | (−0.1-0.34) |
| Median Rate of | 0.12 | 0.11 |
| Lesion Movement | (0.03-1.11) | (0.01-1.26) |
| Magnitude (mm/year) | | |

Comparisons between MS and SVD lesions and lesions having increasing and decreasing volumes was performed with a statistical analysis using RStan in R. The statistical analysis used a Bayesian multivariate multiple linear mixed effects model to control for differences such as patient age, race, ethnicity, and disease duration and the hemisphere in which the lesion was located. Independent subject-specific random effects were performed to capture intra-subject correlations. All models were run for 5,000 warmup iterations and 10,000 post-warmup iterations. After determining convergence to a stationary distribution using three chains, model assumptions were verified using posterior predictive checks. Comparisons were performed and Sidak-adjusted Bayesian p-values were calculated to account for multiple comparisons.

The statistical analysis showed that, for MS lesions assessed using the T2-weighted 3D MRI images, those whose volume increased were 65% less likely to move toward the center of the scan (p=0.01), while those whose volume decreased were 5.3 times more likely to move toward the center of the scan than away from the center of the scan (p<0.0001). However, when assessed using the T1-weighed 3D MRI images, there was no statistically-significant relationship between an MS lesion's change in volume and its displacement toward or away from the center of the scan. Nevertheless, 85% of MS lesions that, from the T2-weighted 3D MRI images, moved away from the center of the scan had expanding volumes as determined using the T1-weighted 3D MRI images. And an MS lesion having an increase in volume as determined from the T2-weighted 3D MRI images was associated with an increase in the lesion volume as determined from the T1-weighted 3D MRI images. For SVD lesions, there was no statistically-significant relationship between a lesion's change in volume and whether it displaced toward or away from the center of the scan under the multivariate statistical model. Under the univariate model, however, an SVD lesion was more likely to move toward the center of the scan if its volume increased (p<0.01), the opposite relationship of the MS lesions.

The statistical analysis also showed that, when measured from the T2-weighted 3D MRI images, the magnitude of displacement of the MS lesions tended to be higher than that of the SVD lesions (p=0.03 for increasing-volume lesions and p=0.003 for decreasing-volume lesions). Additionally, when measured from the T2-weighted 3D MRI images, increasing-volume MS lesions were more likely to have an initial positive x-value position than decreasing-volume MS lesions (p=0.02) and increasing-volume SVD lesions (p=0.03). No other significant differences related to initial lesion positioning were observed between groups. For the rate of displacement, T2-hyperintense, increasing-volume MS lesions were more likely to exhibit a higher displacement rate along the y-axis than T2-hyperintense, decreasing-volume MS lesions (p=0.01). T2-hyperintense lesions positioned at the back of the head (positive x-value position) were more likely to move toward the front of the head (negative x-value displacement) (p<0.0001) and vice versa, and T2 hyperintense lesions positioned at the bottom of the head (negative y-value position) were more likely to move toward the top of the head (positive y-value displacement) (p=0.0004) and vice versa. Meanwhile, T2-hyperintense lesions positioned in the left hemisphere (positive z-value position) were more likely to move toward the left ear (positive z-value displacement) (p<0.0001).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of analyzing one or more lesions of a brain of a patient, the method comprising:

for each of the lesion(s):

from data taken at a first time and data taken at a second time that is after the first time, determining two or more lesion characteristics that include:

a change, from the first time to the second time, in a volume of the lesion; and whether, from the first time to the second time, the lesion moved toward a center of the brain;

assessing whether one or more criteria are satisfied, the one or more criteria including a volume-and-displacement-based criterion that is satisfied when from the determination of the lesion characteristics:

the change in the volume of the lesion is less than zero and the lesion moved toward the center of the brain; or the change in the volume of the lesion is greater than zero and the lesion did not move toward the center of the brain; and characterizing whether the patient has multiple sclerosis and/or the progression, regression, or stability of multiple sclerosis in the patient based at least in part on the assessment of the one or more criteria for each of the lesion(s).

2. The method of claim 1, wherein, for each of the lesion(s), determining whether the lesion moved toward the center of the brain comprises:

calculating a dot product between first and second vectors, wherein:

the first vector extends from a centroid of the lesion at the first time to a centroid of the lesion at the second time; and the second vector extends from the centroid of the lesion at the second time to the center of the brain; and if the dot product is:

greater than zero, determining that the lesion moved toward the center of the brain; and less than zero, determining that the lesion did not move toward the center of the brain.

3. The method of claim 2, wherein the calculating comprises dividing the dot product by the magnitude of the second vector.

4. The method of claim 1, wherein for each of the lesion(s):

the lesion characteristics further include a rate of displacement of a centroid of the lesion from the first time to the second time; and the one or more criteria comprise two or more criteria that further include a displacement-rate-based criterion that is satisfied when from the determination of lesion characteristics a magnitude of the rate of displacement is greater than a threshold rate of displacement.

5. The method of claim 4, wherein the threshold rate of displacement is greater than or equal to 0.16 mm per year.

6. The method of claim 1, wherein:

the data taken at the first time and the data taken at the second time each includes one or more magnetic resonance imaging (MRI) images of the brain of the patient that comprise a 3D representation of each of the lesion(s); and for each of the lesion(s), the change in the volume of the lesion and whether the lesion moved toward the center of the brain are determined from the 3D representations of the lesion.

7. The method of claim 6, wherein for each of the data taken at the first time and the data taken at the second time, the MRI image(s) each is a T2-weighted MRI image.

8. The method of claim 7, wherein:

the data taken at the first time and the data taken at the second time each further includes one or more T1-weighted MRI images that comprise a 3D representation of each of the lesion(s); and for each of the lesion(s):

the change in the volume of the lesion is a first change in the volume of the lesion;

the lesion characteristics include a second change, from the first time to the second time, in a volume of the lesion, the second change in the volume of the lesion determined from the 3D representations of the lesion from the T1-weighted MRI images; and the one or more criteria comprise two or more criteria that further include a volume-based criterion that is satisfied when each of the first and second changes in the volume of the lesion is greater than zero.

9. The method of claim 8, wherein characterizing whether the patient has multiple sclerosis comprises determining that the patient has multiple sclerosis when at least one of the one or more criteria is satisfied for at least a majority of the lesion(s).

10. The method of claim 9, wherein the time elapsed between the first and second times is between 6 months and 4 years.

11. A system for analyzing one or more lesions of a brain of a patient, the system comprising one or more processors configured to:

for each of the lesion(s):

from data taken at a first time and data taken at a second time that is after the first time, determine two or more lesion characteristics that include:

a change, from the first time to the second time, in a volume of the lesion; and whether, from the first time to the second time, the lesion moved toward a center of the brain; and assess whether one or more criteria are satisfied, the one or more criteria including a volume-and-displacement-based criterion that is satisfied when from the determination of the lesion characteristics:

the change in the volume of the lesion is less than zero and the lesion moved toward the center of the brain; or the change in the volume of the lesion is greater than zero and the lesion did not move toward the center of the brain; and characterize whether the patient has multiple sclerosis and/or the progression, regression, or stability of multiple sclerosis in the patient based at least in part on the assessment of the one or more criteria for each of the lesion(s).

12. The system of claim 11, wherein, for each of the lesion(s), the processor(s) are configured to determine whether the lesion moved toward the center of the brain by:

calculating a dot product between first and second vectors, wherein:

the first vector extends from a centroid of the lesion at the first time to a centroid of the lesion at the second time; and the second vector extends from the centroid of the lesion at the second time to the center of the brain; and if the dot product is:

greater than zero, determining that the lesion moved toward the center of the brain; and less than zero, determining that the lesion did not move toward the center of the brain.

13. The system of claim 12, wherein the calculating comprises dividing the dot product by the magnitude of the second vector.

14. The system of claim 13, wherein for each of the lesion(s):

the lesion characteristics further include a rate of displacement of a centroid of the lesion from the first time to the second time; and the one or more criteria comprise two or more criteria that further include a displacement-rate-based criterion that is satisfied when from the determination of lesion characteristics a magnitude of the rate of displacement is greater than a threshold rate of displacement.

15. The system of claim 14, wherein the threshold rate of displacement is greater than or equal to 0.16 mm per year.

16. The system of claim 11, wherein:

the data taken at the first time and the data taken at the second time each includes one or more magnetic resonance imaging (MRI) images of the brain of the patient that comprise a 3D representation of each of the lesion(s); and for each of the lesion(s), the processor(s) are configured to determine the change in the volume of the lesion and whether the lesion moved toward the center of the brain from the 3D representations of the lesion.

17. The system of claim 16, wherein for each of the data taken at the first time and the data taken at the second time, the MRI image(s) each is a T2-weighted 3D MRI image.

18. The system of claim 17, wherein:

the data taken at the first time and the data taken at the second time each further includes a one or more T1-weighted MRI images that comprise a 3D representation of each of the lesion(s); and for each of the lesion(s):

the change in the volume of the lesion is a first change in the volume of the lesion;

the lesion characteristics include a second change, from the first time to the second time, in a volume of the lesion, the second change in the volume of the lesion determined from the 3D representations of the lesion from the T1-weighted MRI images; and the one or more criteria comprise two or more criteria that further include a volume-based criterion that is satisfied when each of the first and second changes in the volume of the lesion is greater than zero.

19. The system of claim 11, wherein the processor(s) are configured to characterize whether the patient has multiple sclerosis by determining that the patient has multiple sclerosis when at least one of the one or more criteria is satisfied for at least a majority of the lesion(s).

* * * * *